US012403314B2

(12) United States Patent
Kramer et al.

(10) Patent No.: US 12,403,314 B2
(45) Date of Patent: Sep. 2, 2025

(54) NEUROSTIMULATION USING TIME-INTERLEAVED CASCADE OF BIPOLAR ELECTRODE COMBINATIONS

(71) Applicant: Medtronic, Inc., Minneapolis, MN (US)

(72) Inventors: Jeffery M. Kramer, St. Louis Park, MN (US); Andrew J. Cleland, St. Paul, MN (US); Leonid M. Litvak, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 644 days.

(21) Appl. No.: 17/652,245

(22) Filed: Feb. 23, 2022

(65) Prior Publication Data

US 2022/0266029 A1  Aug. 25, 2022

Related U.S. Application Data

(60) Provisional application No. 63/153,201, filed on Feb. 24, 2021.

(51) Int. Cl.
*A61N 1/36* (2006.01)
*A61N 1/05* (2006.01)
*A61N 1/372* (2006.01)

(52) U.S. Cl.
CPC ........... *A61N 1/36139* (2013.01); *A61N 1/05* (2013.01); *A61N 1/36192* (2013.01); *A61N 1/37235* (2013.01); *A61N 1/36062* (2017.08); *A61N 1/36064* (2013.01); *A61N 1/36067* (2013.01); *A61N 1/36071* (2013.01); *A61N 1/36107* (2013.01)

(58) Field of Classification Search
CPC .. A61N 1/36139; A61N 1/05; A61N 1/37235; A61N 1/36062; A61N 1/36064; A61N 1/36067; A61N 1/36071; A61N 1/36107
USPC ............................................................ 607/2
See application file for complete search history.

(56) References Cited

U.S. PATENT DOCUMENTS

| | | | |
|---|---|---|---|
| 6,463,328 B1 * | 10/2002 | John | G16H 20/17 607/45 |
| 7,881,805 B2 | 2/2011 | Bradley et al. | |
| 8,923,976 B2 | 12/2014 | Johanek | |
| 9,533,154 B2 | 1/2017 | Kothandaraman et al. | |

(Continued)

FOREIGN PATENT DOCUMENTS

| | | |
|---|---|---|
| DE | 102008024972 A1 | 12/2009 |
| EP | 3623004 A1 | 3/2020 |

OTHER PUBLICATIONS

International Search Report and Written Opinion of International Application No. PCT/US2022/070823, dated May 30, 2022, 13 pp.

*Primary Examiner* — Mallika D Fairchild
(74) *Attorney, Agent, or Firm* — Shumaker & Sieffert, P.A.

(57) ABSTRACT

An example method of delivering electrical stimulation includes obtaining, by an implantable medical device (IMD) connected to a lead carrying a plurality of electrodes, one or more stimulation parameters; and delivering, by the IMD and based on the one or more stimulation parameters, electrical stimulation therapy via the plurality of electrodes, wherein delivering the electrical stimulation therapy comprises scanning delivery of the electrical stimulation therapy through different pairs of electrodes of the plurality of electrodes.

20 Claims, 8 Drawing Sheets

(56) References Cited

U.S. PATENT DOCUMENTS

| | | |
|---|---|---|
| 10,525,268 B2 | 1/2020 | Torgerson |
| 2006/0190057 A1 | 8/2006 | Reese |
| 2006/0229687 A1 | 10/2006 | Goetz et al. |
| 2007/0203540 A1 | 8/2007 | Goetz et al. |
| 2013/0261706 A1 | 10/2013 | Mirro et al. |
| 2013/0289664 A1 | 10/2013 | Johanek |
| 2017/0080233 A1 | 3/2017 | Torgerson et al. |
| 2018/0056073 A1 | 3/2018 | Torgerson |
| 2019/0209833 A1* | 7/2019 | Kim .................. A61N 1/36185 |
| 2022/0241587 A1* | 8/2022 | Grahn .................. A61N 1/0551 |
| 2023/0128146 A1* | 4/2023 | Huertas Fernandez ..................... A61N 1/36132 607/59 |

\* cited by examiner

NEUROSTIMULATION USING TIME-INTERLEAVED CASCADE OF BIPOLAR ELECTRODE COMBINATIONS

This application claims the benefit of U.S. Provisional Patent Application No. 63/153,201, filed 24 Feb. 2021, the entire contents of which is incorporated herein by reference.

TECHNICAL FIELD

This disclosure generally relates to medical devices, and more specifically, electrical stimulation.

BACKGROUND

Electrical stimulation devices, sometimes referred to as neurostimulators or neurostimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads, positioned proximate to target locations associated with the brain, the spinal cord, pelvic nerves, tibial nerves, peripheral nerves, the gastrointestinal tract, or elsewhere within a patient. Stimulation proximate the spinal cord, proximate the sacral nerve, within the brain, and proximate peripheral nerves is often referred to as spinal cord stimulation (SCS), sacral neuromodulation (SNM), deep brain stimulation (DBS), and peripheral nerve stimulation (PNS), respectively.

A physician or clinician may select values for a number of programmable stimulation parameters in order to define the electrical stimulation therapy to be delivered by the implantable stimulator to a patient. For example, the physician or clinician may select one or more electrodes, polarities of selected electrodes, a voltage or current amplitude, a pulse width, and a pulse frequency as stimulation parameters. A set of therapy stimulation parameters, such as a set including electrode combination, electrode polarity, amplitude, pulse width and pulse frequency, may be referred to as a therapy program in the sense that they define the electrical stimulation therapy to be delivered to the patient.

SUMMARY

In general, the disclosure describes techniques for delivering neurostimulation using a time-interleaved cascade of bipolar electrode combinations. When delivering neurostimulation, it may be desirable to select electrodes that are most proximate to a stimulation target. For instance, when delivering neurostimulation to a spinal cord of a patient, it may be desirable to deliver electrical stimulation via electrodes that are most proximate to a nerve root of the spinal cord. However, various circumstances may make it difficult to determine which electrodes are most proximate to the simulation target. As one example, the simulation target may be relatively small (e.g., with reference to a lead that carries the electrodes). As another example, movement of the patient may result in relative movement between the electrodes and the stimulation target. When electrical stimulation does not reach the stimulation target, treatment may not be successful. Additionally, sporadic reaching of electrical stimulation to the stimulation target may be distracting to the patient.

In accordance with one or more techniques of this disclosure, an implantable medical device (IMD) may deliver electrical stimulation via a time-interleaved cascade of bipolar electrode combinations. For instance, as opposed to continuously delivering electrical stimulation via a particular pair of electrodes, the IMD may scan through a plurality of pairs of electrodes when delivering electrical stimulation. The pairs of electrodes may include different pairs, in which at least one electrode in a pair is at a different position than an electrode in at least one other pair. As one example, the IMD may deliver electrical stimulation via a first pair of electrodes at a first time, deliver electrical stimulation via a second pair of electrodes at a second time, and deliver stimulation via a third pair of electrodes at a third time. A scan frequency (e.g., a frequency at which the IMD switches between electrode pairs) may be selected such that the scanning is imperceptible to the patient (e.g., greater than 20 Hz, greater than 30 Hz, greater than 45 Hz, etc.). In this way, the IMD may effectively deliver stimulation to a larger area such that the stimulation has a greater probability of hitting the stimulation target.

As one example, a method of delivering electrical stimulation includes: obtaining, by an implantable medical device (IMD) connected to a lead carrying a plurality of electrodes, one or more stimulation parameters; and delivering, by the IMD and based on the one or more stimulation parameters, electrical stimulation therapy via the plurality of electrodes, wherein delivering the electrical stimulation therapy comprises scanning delivery of the electrical stimulation therapy through different pairs of electrodes of the plurality of electrodes.

As another example, a system includes a memory storing one or more stimulation parameters; and an implantable medical device comprising processing circuitry configured to obtain the one or more stimulation parameters; and deliver, based on the one or more stimulation parameters and via a plurality of electrodes carried by a lead, electrical stimulation therapy, wherein delivering the electrical stimulation therapy comprises scanning delivery of the electrical stimulation therapy through different pairs of electrodes of the plurality of electrodes.

The details of one or more examples are set forth in the accompanying drawings and the description below. Other features, objects, and advantages will be apparent from the description, drawings, and claims.

DETAILED DESCRIPTION

Figure 1:
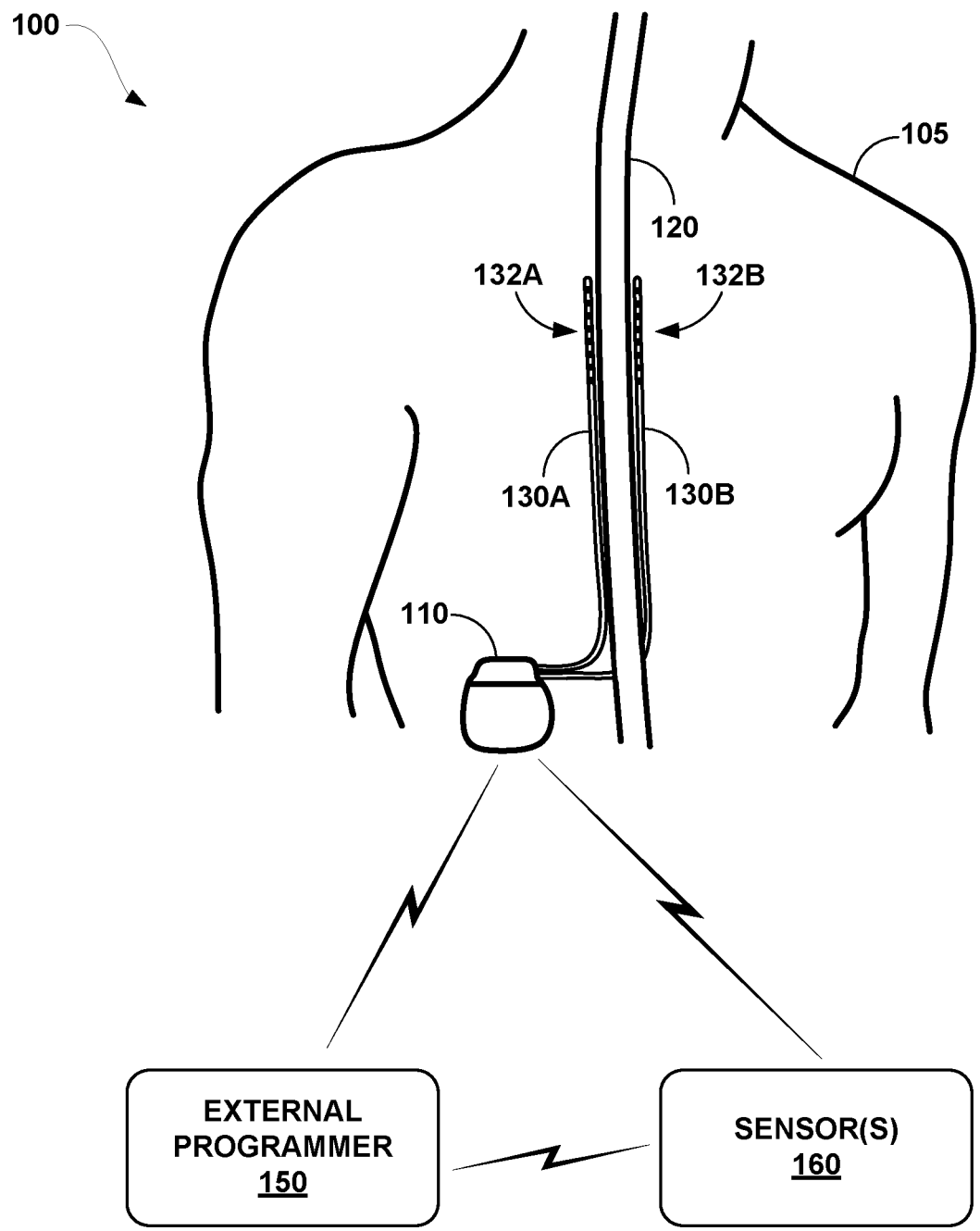
FIG. 1 is a conceptual diagram illustrating an example system that includes an implantable medical device (IMD) in the form of a neurostimulation device configured to deliver spinal cord stimulation (SCS), an external programmer, and one or more sensing devices in accordance with one or more techniques of this disclosure.

FIG. 1 is a conceptual diagram illustrating an example system 100 that includes an implantable medical device (IMD) 110 configured to deliver spinal cord stimulation (SCS) therapy, processing circuitry 140, an external programmer 150, and one or more sensors 160, in accordance with one or more examples of this disclosure. Processing circuitry 140 may include one or more processors configured to perform various operations of IMD 110. Although the examples described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of neurostimulation devices or other therapeutic applications of neurostimulation, including an external neurostimulator. For example, the system may not be a fully implanted system where the pulse generator is external to the patient and stimulation is transmitted transdermally. In one or more examples, the stimulators may be configured to deliver peripheral nerve stimulation or spinal nerve root stimulation.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105, e.g., for relief of chronic pain or other symptoms, via one or more electrodes 132A, 132B of leads 130A and/or 130B, respectively. In the example of FIG. 1, each lead 130A, 130B includes eight electrodes 132A, 132B respectively, although the leads may each have a different number of electrodes. Leads 130A, 130B may be referred to collectively as "leads 130" and electrodes 132A, 132B may be referred to collectively as "electrodes 132." In other examples, IMD 110 may be coupled to a single lead carrying multiple electrodes or more than two leads each carrying multiple electrodes.

IMD 110 may be a chronic electrical stimulator that remains implanted within patient 105 for weeks, months, or years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to one or more leads percutaneously implanted within the patient. In some examples, IMD 110 uses electrodes on one or more leads, while in other examples, IMD 110 may use one or more electrodes on a lead or leads and one of more electrodes on a housing of the IMD. In further examples, IMD 110 may be leadless and instead use only electrodes carried on a housing of the IMD.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted at other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

In the example of FIG. 1, electrical stimulation energy, which may be delivered as regulated current or regulated voltage-based pulses, is delivered from IMD 110 to one or more target tissue sites of patient 105 via leads 130 and electrodes 132. Leads 130 position electrodes 132 adjacent to target tissue of spinal cord of patient 105. One or more of the electrodes 132 may be disposed at a distal tip of a lead 130 and/or at other positions at intermediate points along the lead. Leads 130 may be implanted and coupled to IMD 110. The electrodes 132 may transfer electrical stimulation generated by an electrical stimulation generator in IMD 110 to tissue of patient 105. Although leads 130 may each be a single lead, a lead 130 may include a lead extension or other segments that may aid in implantation or positioning of lead 130.

The electrodes 132 of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration. Deployment of electrodes via leads 130 is described for purposes of illustration, but electrodes may be arranged on a housing of IMD 110, e.g., in rows and/or columns (or other arrays or patterns), as surface electrodes, ring electrodes, or protrusions.

Neurostimulation stimulation parameters defining the electrical stimulation pulses delivered by IMD 110 through electrodes 132 of leads 130 may include information identifying which electrodes have been selected for delivery of the stimulation pulses according to a stimulation program and the polarities of the selected electrodes (the electrode combination), and voltage or current amplitude, pulse rate (i.e., frequency), and pulse width of the stimulation pulses. The neurostimulation stimulation parameters may further include a cycling parameter that specifies when, or how long, stimulation is turned on and off. Neurostimulation stimulation parameters may be programmed prior to delivery of the neurostimulation pulses, manually adjusted based on user input, or automatically controlled during delivery of the neurostimulation pulses, e.g., based on sensed conditions.

Although the example of FIG. 1 is directed to SCS therapy, e.g., to treat pain, in other examples, system 100 may be configured to treat other conditions that may benefit from neurostimulation therapy. For example, system 100 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, or anxiety disorders. Hence, in some examples, system 100 may be configured to deliver sacral neuromodulation (SNM), deep brain stimulation (DBS), peripheral nerve stimulation (PNS), or other stimulation, such as peripheral nerve field stimulation (PNFS), cortical stimulation (CS), gastrointestinal stimulation, or any other stimulation therapy capable of treating a condition of patient 105. In some examples, system 100 may be configured where the electrical stimulation includes stimulation parameters to deliver therapy to address a condition of one or more of painful diabetic neuropathy (PDN), peripheral vascular disease (PVD), peripheral artery disease (PAD), complex regional pain syndrome (CRPS), angina pectoris (AP), leg pain, back pain or pelvic pain.

Leads 130 may include, in some examples, one or more sensors configured to sense one or more physiological stimulation parameters of patient 105, such as patient activity, pressure, temperature, posture, heart rate, blood flow, or other characteristics. At least some of electrodes 132 may be used to sense electrical signals within patient 105, additionally or alternatively to delivering stimulation. IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in any suitable region, such as the thoracic, cervical or lumbar regions.

Stimulation of spinal cord 120 may, for example, prevent pain signals from being generated and/or traveling through spinal cord 120 and to the brain of patient 105. Patient 105 may perceive the interruption of pain signals as a reduction in pain and, therefore, efficacious therapy results. In some examples, stimulation of spinal cord 120 may produce paresthesia which may reduce the perception of pain by patient 105, and thus, provide efficacious therapy results. In other examples, stimulation of spinal cord 120 may be effective in reducing pain with or without presenting paresthesia. In some examples, some electrical stimulation pulses may be directed to glial cells while other electrical stimulation (e.g., delivered by a different electrode combination and/or with different stimulation parameters) is directed to neurons. In other examples, stimulation of spinal cord 120 may be effective in promoting blood flow in one or more remote tissue locations, e.g., in a limb or appendage, thereby alleviating or reducing pain or other symptoms, or preventing or delaying onset of tissue damage or degeneration.

IMD 110 generates and delivers electrical stimulation therapy to a target stimulation site within patient 105 via the electrodes of leads 130 to patient 105 according to one or more therapy stimulation programs. A therapy stimulation program specifies values for one or more stimulation parameters that define an aspect of the therapy delivered by IMD 110 according to that program. For example, a stimulation therapy program that controls delivery of stimulation by IMD 110 in the form of stimulation pulses may define values for voltage or current pulse amplitude, pulse width, and pulse rate (i.e., pulse frequency) for stimulation pulses delivered by IMD 110 according to that program, as well as the particular electrodes and electrode polarities forming an electrode combination used to deliver the stimulation pulses. Hence, a stimulation therapy program may specify the location(s) at which stimulation is delivered and amplitude, pulse width and pulse rate of the stimulation. In some examples, a stimulation therapy program may specify cycling of the stimulation, e.g., in terms of when, or how long, stimulation is turned on and off.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine, e.g., as a handheld computer similar to a tablet or smartphone. For example, a patient programmer may receive input from patient 105 when the patient wishes to terminate or change stimulation therapy. In general, a physician or clinician programmer may support selection and generation of programs by a clinician for use by IMD 110, and may take the form, for example, of a handheld computer (e.g., a tablet computer), laptop computer or desktop computer, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

IMD 110 and external programmer 150 may exchange information and may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

IMD 110, in response to commands from external programmer 150, may deliver electrical stimulation therapy according to a plurality of therapy stimulation programs to a target tissue site of the spinal cord 120 of patient 105 via electrodes 132 on leads 130. In some examples, IMD 110 automatically modifies therapy stimulation programs as therapy needs of patient 105 evolve over time. For example, the modification of the therapy stimulation programs may cause the adjustment of at least one parameter of the plurality of stimulation pulses based on received information.

IMD 110 and/or external programmer 150 may receive information from one or more sensors 160, e.g., directly via wireless communication or indirectly from an intermediate server via a network connection. Sensor 160 may be positioned to sense one or more physiological responses at a selected location on patient 105. In some examples, sensor 160 may be positioned at, attached to or near tissue for a target anatomical area, e.g., at a limb or appendage, such as at or on a leg, toe, foot, arm, finger or hand of patient 105, e.g., to sense a galvanic skin response adjacent to placement of sensor 160. In some examples, sensor 160 may be attached to an appendage of the patient 105 to sense a physiological response associated with the appendage, e.g., by a clip-on mechanism, strap, elastic band and/or adhesive. In some examples, sensor 160 (or one of a plurality of sensors 160) may be implantable within patient 105, e.g., within a limb or appendage of the patient, near the spinal cord of the patient, within the brain of the patient, and the like.

In some examples, sensor 160 may be a physiological and/or patient posture or behavior sensor. For example, sensor 160 may be a heart rate monitor configured to detect and/or determine a heart rate and/or a heart rate variability. Sensor 160 may be configured to detect and/or determine a galvanic skin response, or to detect and/or determine a biopotential. Sensor 160 may be a thermometer configured to detect and/or determine a temperature of at least a part of the patient's anatomy. Sensor 160 may be configured to measure a pressure, e.g., a patient blood pressure, or to measure an impedance of at least a portion of the patient's anatomy. Sensor 160 may be a blood flow sensor that measures blood flow and provides information related to blood flow associated with tissue of the patient. For example, sensor 160 may provide blood flow values, or other information indicative of blood flow values or changes in blood flow values. The blood flow value may be an instantaneous blood flow measurement or may be a measurement of blood flow over a period of time such as average blood flow value, maximum blood flow value, minimum blood flow value during the period of time. In some examples, sensor 160 may be a microphone configured to detect/determine sounds of at least a portion of the patient's anatomy. In some examples, sensor 160 may at least partially comprise electrodes 132A, 132B. For example, sensor 160 may be configured to detect and/or determine ECAPs, LFPs, a network excitability, and the like. In some examples, sensor 160 may comprise an accelerometer configured to detect and/or determine a position and/or patient movement, a patient movement history over a predetermined amount of time, and the like. In some examples, sensor 160 may be a patient-input device, e.g., external programmer 150, a smartphone or computing device, or any other suitable device, configured to receive and communicate subjective patient feedback. For example, sensor 160 may be configured to receive a pain response, a pain score, an area of pain, an amount of paresthesia, an area of paresthesia, information relating to voiding and/or a voiding rate (e.g., voids per day), and the like. In some examples, sensor 160 may be an environmental sensor, such as a microphone, thermometer, hygrometer, pressure sensor, and the like, configured to detect and/or determine sounds, temperatures, humidity and pressure, etc., of the environment in which the patient is located.

When delivering neurostimulation, it may be desirable for IMD 110 to deliver electrical stimulation via electrodes that are most proximate to a stimulation target. For instance, when delivering neurostimulation to spinal cord 120 of patient 105, it may be desirable for IMD 110 to deliver electrical stimulation via electrodes of electrodes 132A/132B that are most proximate to a nerve root of spinal cord 120. However, various circumstances may make it difficult to determine which electrodes of electrodes 132A/132B are most proximate to the simulation target. As one example, the simulation target may be relatively small (e.g., with reference to a lead that carries the electrodes). As another example, movement of patient 105 may result in relative movement between electrodes 132A/132B and the stimulation target. When electrical stimulation does not reach the stimulation target, treatment may not be successful. Additionally, sporadic reaching of electrical stimulation to the stimulation target may be distracting to patient 105.

In accordance with one or more techniques of this disclosure, IMD 110 may deliver electrical stimulation via a time-interleaved cascade of bipolar electrode combinations. For instance, as opposed to continuously delivering electrical stimulation via a particular pair of electrodes of electrodes 132A/132B, IMD 110 may scan through a plurality of different pairs of electrodes 132A/132B when delivering electrical stimulation. As one example, IMD 110 may deliver electrical stimulation via a first pair of electrodes 132A/132B at a first time, deliver electrical stimulation via a second pair of electrodes 132A/132B at a second time, and deliver stimulation via a third pair of electrodes 132A/132B at a third time. The pairs of electrodes may have an electrode in common. The pairs of electrodes may include different pairs, in which at least one electrode in a pair is at a different position than an electrode in at least one other pair. A scan frequency (e.g., a frequency at which IMD 110 switches between electrode pairs) may be selected such that the scanning is imperceptible to the patient (e.g., greater than 20 Hz, greater than 30 Hz, greater than 45 Hz, etc.). In this way, IMD 110 may effectively deliver stimulation to a larger area such that the stimulation has a greater probability of hitting the stimulation target. Even though stimulation is effectively being delivered to a larger area, an amount of energy consumed for delivery of the stimulation may not be significantly increased.

Figure 2:
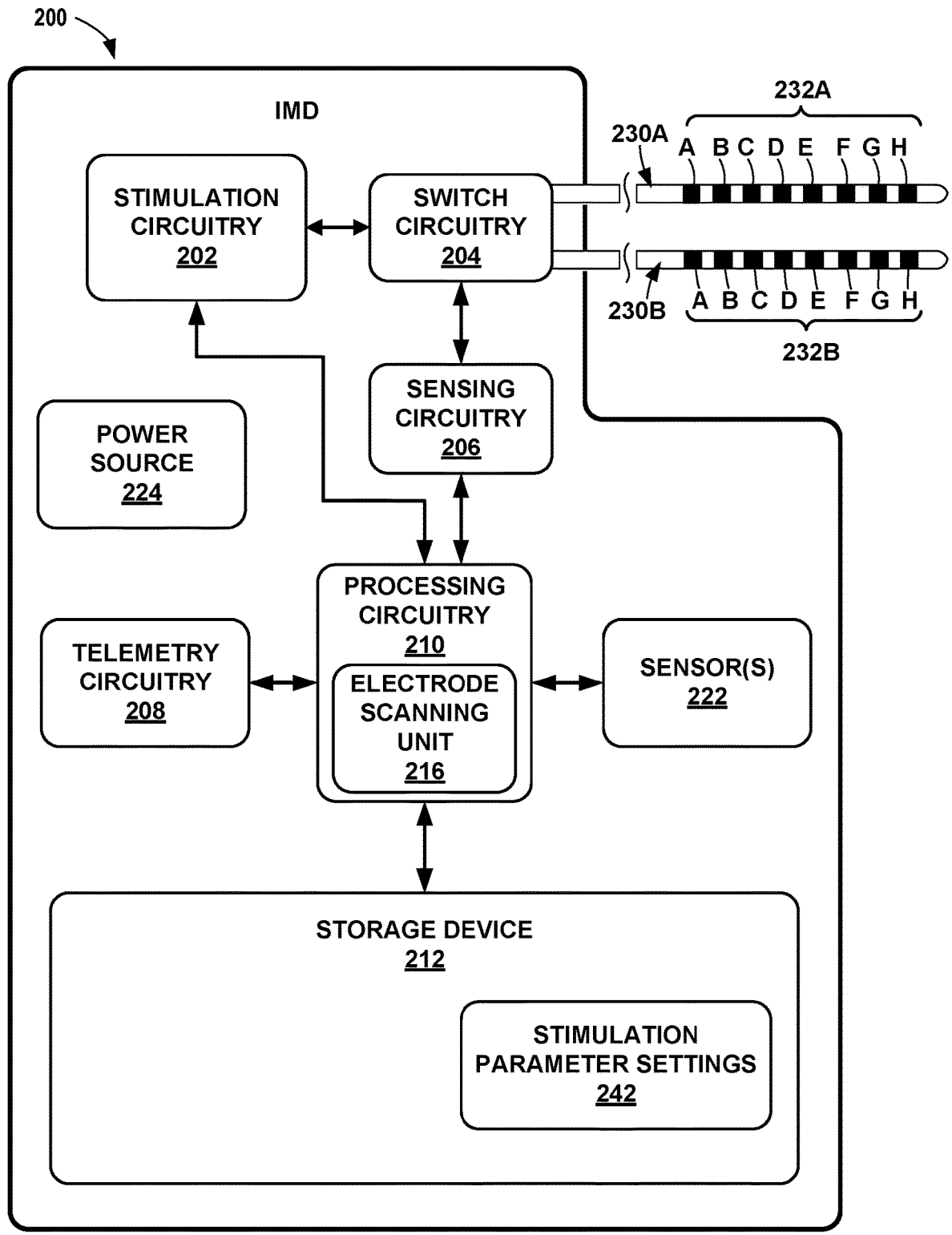
FIG. 2 is a block diagram illustrating an example of an IMD in the form of a neurostimulation device, in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 may include stimulation generation circuitry 202, switch circuitry 204, sensing circuitry 206, telemetry circuitry 208, sensor(s) 222, lead 230A carrying electrodes 232A, which may correspond to lead 130A and electrodes 132A of FIG. 1, and lead 230B carrying electrodes 232B, which may correspond to lead 130B and electrodes 132B of FIG. 1. In the example shown in FIG. 2, IMD 200 includes processing circuitry 210, power source 224, and storage device 212. Processing circuitry 210 may include one or more processors configured to perform various operations of IMD 200. In the examples shown in FIG. 2, storage device 212 may store stimulation parameter settings 242.

Stimulation generation circuitry 202 includes electrical stimulation circuitry configured to generate electrical stimulation pulses selected to alleviate symptoms of one or more diseases, disorders or syndromes. While stimulation pulses are described, stimulation signals may take other forms, such as continuous-time signals (e.g., sine waves) or the like. The electrical stimulation circuitry may reside in an implantable housing, for example, of the IMD. Each of leads 230A, 230B may include any number of electrodes 232A, 232B. The electrodes are configured to deliver the electrical stimulation to the patient. In the example of FIG. 2, each set of electrodes 232A, 232B includes eight electrodes A-H. In some examples, the electrodes are arranged in bipolar combinations. A bipolar electrode combination may use electrodes carried by the same lead 230A, 230B or different leads. For example, an electrode A of electrodes 232A may be a cathode and an electrode B of electrodes 232A may be an anode, forming a bipolar combination. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. Current may be sourced or sunk by electrodes such that an electrode may selectively form an anode or a cathode. In particular, in some examples, each of the electrodes 232A, 232B may be associated with respective regulated current source and sink circuitry to selectively and independently configure the electrode to be a regulated cathode or anode. Stimulation generation circuitry 202 and/or sensing circuitry 206 also may include sensing circuitry to direct electrical signals sensed at one or more of electrodes 232A, 232B.

Sensing circuitry 206 may be configured to monitor signals from any combination of electrodes 232A, 232B. In some examples, sensing circuitry 206 includes one or more amplifiers, filters, and analog-to-digital converters. Sensing circuitry 206 may be used to sense physiological signals, such as ECAP signals and/or LFP signals. In some examples, sensing circuitry 206 detects ECAP and/or LFP signals from a particular combination of electrodes 232A, 232B. In some cases, the particular combination of electrodes for sensing ECAP and/or LFP signals includes different electrodes than a set of electrodes 232A, 232B used to deliver stimulation pulses. Alternatively, in other cases, the particular combination of electrodes used for sensing ECAP and/or LFP signals includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer or another computing device under the control of processing circuitry 210. Processing circuitry 210 of IMD 200, respectively, may receive, as updates to programs, values for various stimulation parameters such as amplitude and electrode combination, from the external programmer via telemetry circuitry 208. Processing circuitry 210 of IMD 200 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer via proximal inductive interaction of IMD 200 with the external programmer, where the external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include one or more processors, such as any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242. In some examples, processing circuitry 210 may execute other instructions stored in storage device 212, respectively, to apply stimulation parameters specified by one or more of programs, such as amplitude, pulse width, pulse rate, and pulse shape of each of the stimulation signals.

In the illustrated example of FIG. 2, processing circuitry 210 includes an electrode scanning unit 216 that may be configured to control delivery of electrical stimulation by scanning through pairs of electrodes. Electrode scanning unit 216 may be implemented as any combination of hardware and software.

Storage device 212 may be configured to store information within IMD 200, respectively, during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions, e.g., for execution by processing circuitry 210, respectively. As discussed above, storage device 212 is configured to store stimulation parameter settings 242.

Power source 224 may be configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium-ion batteries. In some examples, power sources 224 may be primary cell devices.

Processing circuitry 210 controls stimulation circuitry 202 to deliver stimulation energy with stimulation parameters specified by one or more stimulation parameter settings 242 stored on storage device 212.

Figure 3:
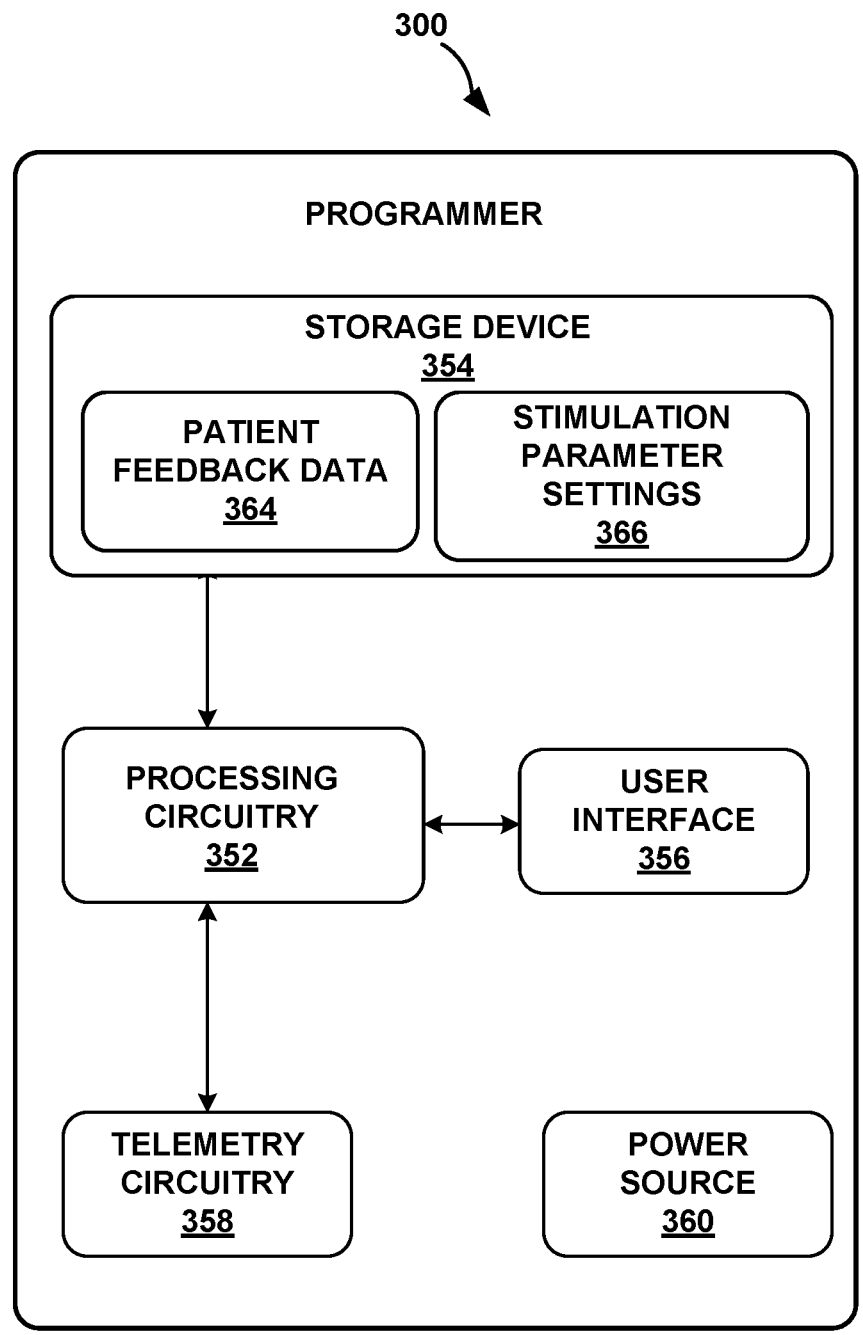
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, such as a tablet computer or smartphone-like device, external programmer 300 may be a larger portable device, such as a laptop computer, or a more stationary device, such as a desktop computer. In addition, in other examples, external programmer 300 may be included as part of an external charging device or include the functionality of an external charging device, e.g., to recharge a battery or batteries associated with IMD 200. As illustrated in FIG. 3, external programmer 300 may include processing circuitry 352, storage device 354, user interface 356, telemetry circuitry 358, and power source 360. In some examples, storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, processing circuitry 352, telemetry circuitry 358, or other circuitry of external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated, either partially or entirely. In some examples, processing circuitry 352, telemetry circuitry 358 or other circuitry of external programmer 300 may correspond to individual hardware units, such as ASICs, DSPs, FPGAs, or other hardware units.

The processing circuitry 352 is configured to direct delivery of electrical stimulation, receive information relating patient feedback. In some examples, the processing circuitry 352 is configured to control the electrical stimulation circuitry by directing the IMD to use particular stimulation parameters.

Storage device 354 (e.g., a storage device) may, in some examples, store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory or receive user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110) and/or a remote sensing device. For example, storage device 354 may store data recorded at a sensing module of the medical device, and storage device 354 may also store data from one or more sensors of the medical device. In an example, storage device 354 may store data recorded at a remote sensing device such as patient feedback from one or more sensors and/or patient-input devices.

User interface 356 may include a button or keypad, lights, a speaker for voice commands, a display, such as a liquid crystal (LCD), light-emitting diode (LED), or organic light-emitting diode (OLED). In some examples, the display includes a touch screen. User interface 356 may be configured to display any information related to the delivery of electrical stimulation including output. User interface 356 may also receive user input (e.g., indication of when the patient perceives stimulation, or a pain score perceived by the patient upon delivery of stimulation) via user interface 356. The user input may be, for example, in the form of pressing a button on a keypad or selecting an icon from a touch screen. The input may request starting or stopping electrical stimulation, the input may request a new electrode combination or a change to an existing electrode combination, or the input may request some other change to the delivery of electrical stimulation, such as a change in stimulation cycling amplitude, pulse width or pulse rate.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameters to IMD 110 for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

In some examples, the external programmer 300 or external control device directs delivery of electrical stimulation by an IMD, receives information relating to patient feedback, and generates output based on the received information, e.g., for evaluation of efficacy of stimulation parameters and/or to recommend or assist a user in programming stimulation parameters for delivery of electrical stimulation, or used as part of a closed loop control device to automatically adjust stimulation parameters using patient feedback information.

Programmer 300 may be a patient programmer or a clinician programmer and receives patient feedback information such as patient feedback data 364. Programmer 300 receives patient feedback information and allows a user to interact with the processing circuitry 352 via user interface 356 in order to identify efficacious parameter settings, such as cycling and/or one or more other stimulation parameters using the patient feedback information. Programmer 300 further assists the user in programming a neurostimulation device by using the patient feedback information displayed on the user interface 356.

In an example, programmer 300 may be used to cause the IMD to automatically scan though a plurality of electrode combinations or parameter combinations. Processing circuitry 352 causes the IMD to automatically scan through each of a plurality of parameter combinations, including electrode combinations and parameter combinations.

Alternative to or in addition to the automatic scanning process, the user could manually advance scanning through electrode pairs and/or parameter combinations, for example with an arrow button on user interface 356. In some examples, as the user scans through the electrode pairs or parameter combinations to test and record patient feedback for each combination, the user may collect information such as a patient pain score indicating the degree of pain relief information from the combination, or a stimulation perception score indicating whether the patient perceives the stimulation, e.g., by verbal interaction with the patient or patient entry of information via a user input device, and enter the pain information into programmer 300 via user interface 356 of the programmer or the user input device.

In some examples, the processing circuitry 352 of programmer 300 directs delivery of electrical stimulation of the electrodes 232A, 232B, and receives information relating to patient feedback, and controls the delivery of electrical stimulation of the electrodes 232A, 232B based on the received patient feedback information in a closed loop setting. The patient feedback information may be received via the telemetry circuitry 358 either directly or indirectly from sensor 160 (FIG. 1) and/or a patient-input device.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
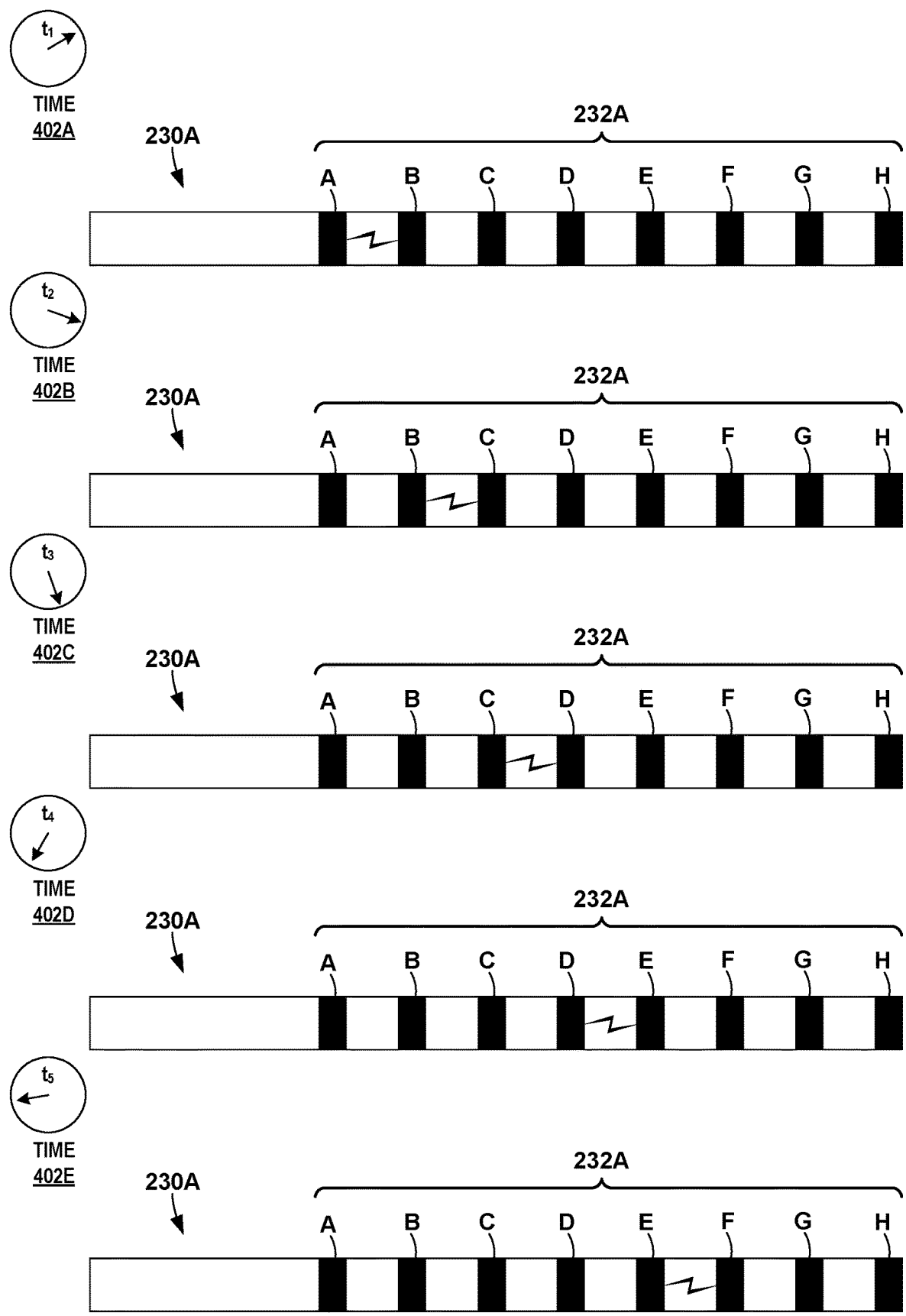
FIGS. 4 and 5 are conceptual diagrams illustrating examples of scanning through pairs of electrodes, in accordance with one or more techniques of this disclosure.
Figure 5:
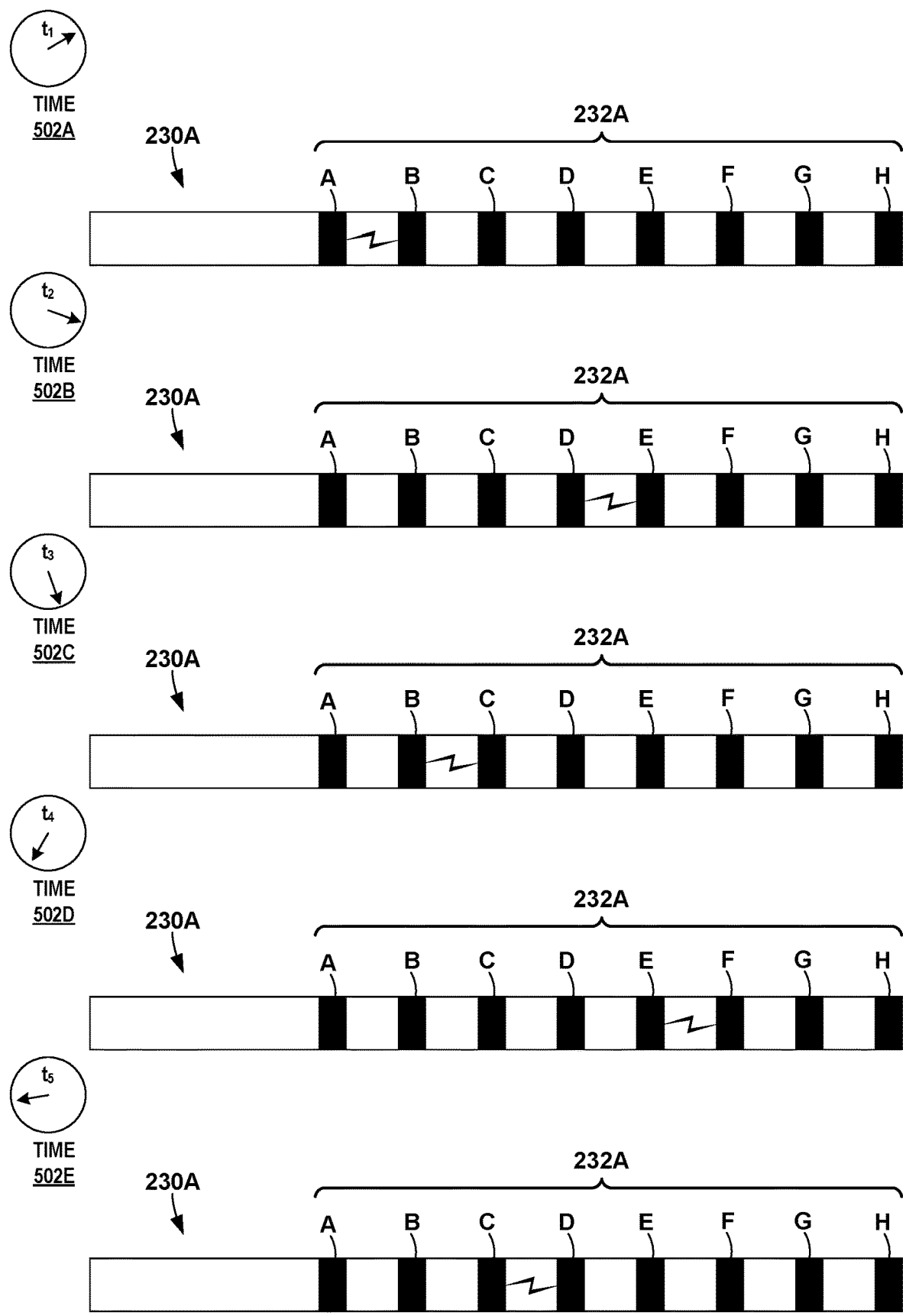

FIGS. 4 and 5 are conceptual diagrams illustrating examples of scanning through pairs of electrodes, in accordance with one or more techniques of this disclosure. FIG. 4 illustrates an example of monotonic scanning. FIG. 5 illustrates an example of non-monotonic scanning.

As noted above, IMD 110 may scan through pairs of electrodes monotonically. For instance, IMD 110 may successively step through electrode pairs along a longitudinal axis of a lead. As shown in FIG. 4, at first time 402A $t_1$, IMD 110 may deliver bipolar electrical stimulation using a first pair of electrodes that includes electrodes A and B of electrodes 232A of lead 230A. At second time 402B $t_2$, IMD 110 may deliver bipolar electrical stimulation using a second pair of electrodes that includes electrodes B and C of electrodes 232A of lead 230A. As such, in some examples, the second pair of electrodes may include an electrode that is included in the first pair of electrodes and an electrode that is not included in the first pair of electrodes. At third time 402C $t_3$, IMD 110 may deliver bipolar electrical stimulation using a third pair of electrodes that includes electrodes C and D of electrodes 232A of lead 230A. At fourth time 402D $t_4$, IMD 110 may deliver bipolar electrical stimulation using a fourth pair of electrodes that includes electrodes D and E of electrodes 232A of lead 230A. At fifth time 402E $t_5$, IMD 110 may deliver bipolar electrical stimulation using a fifth pair of electrodes that includes electrodes E and F of electrodes 232A of lead 230A.

IMD 110 may loop over the pairs of electrodes using the same order or a reverse order. When IMD 110 loops over the pairs of electrodes using the same order, IMD 110 may deliver, at a sixth time after the fifth time, bipolar electrical stimulation using electrodes A and B of electrodes 232A of lead 230A (e.g., followed by electrodes B and C at a sixth time). When IMD 110 loops over the pairs of electrodes using the reverse order (e.g., a serpentine scan), IMD 110 may deliver, at a sixth time after the fifth time, bipolar electrical stimulation using electrodes D and E of electrodes 232A of lead 230A (e.g., followed by electrodes C and D at a seventh time).

The pairs of electrodes may be selected about a central point. For instance, a pair of electrodes including electrodes C and D may be determined to be overlying a stimulation target (e.g., a nerve root). However, as discussed above, delivering electrical stimulation via just electrodes C and D may not result in desired delivery of therapy to the stimulation target (e.g., as the lead may migrate, the patient may move, etc.). Furthermore, while increasing an amplitude of electrical stimulation delivered via electrodes C and D may increase a probability that the stimulation target receives electrical stimulation, such an increase may have undesirable side effects (e.g., increased energy consumption and/or undesired recruitment of other nerves, such as motor neurons, causing possible discomfort). By delivering electrical stimulation including scanning/cascading through pairs of leads, IMD 110 may effectively deliver therapy to a larger area (e.g., increasing a probability that the stimulation target receives electrical stimulation). Also in this way, an implantation tolerance of a lead may be increased (e.g., the surgeon may not have to be as precise).

As noted above, IMD 110 may scan through pairs of electrodes non-monotonically. For instance, IMD 110 may successively step through electrode pairs along a longitudinal axis of a lead, where at least one electrode is "skipped." As shown in FIG. 5, at first time 502A $t_1$, IMD 110 may deliver bipolar electrical stimulation using a first pair of electrodes that includes electrodes A and B of electrodes 232A of lead 230A. At second time 502B $t_2$, IMD 110 may deliver bipolar electrical stimulation using a second pair of electrodes that includes electrodes D and E of electrodes 232A of lead 230A. As such, in some examples, the second pair of electrodes may not include any electrodes that are included in the first pair of electrodes. At third time 502C $t_3$, IMD 110 may deliver bipolar electrical stimulation using a third pair of electrodes that includes electrodes B and C of electrodes 232A of lead 230A. At fourth time 502D $t_4$, IMD 110 may deliver bipolar electrical stimulation using a fourth pair of electrodes that includes electrodes E and F of electrodes 232A of lead 230A. At fifth time 502E $t_5$, IMD 110 may deliver bipolar electrical stimulation using a fifth pair of electrodes that includes electrodes C and D of electrodes 232A of lead 230A.

In some examples, the electrodes scanned through by IMD 110 may be a contiguous block of electrodes. For instance, as shown in FIG. 4, every electrode between and including electrodes A and F may be included in at least one pair of electrodes. In some examples, the electrodes scanned through by IMD 110 may be a non-contiguous block of electrodes. For instance, each of electrodes A-D and F-H may be included in at least one pair of electrodes scanned through by IMD 110 while electrode E may not be included in any of the pairs of electrodes scanned through by IMD 110.

IMD 110 may scan through the pairs of electrodes at a scanning frequency. In some examples, the scanning frequency may be greater than or equal to 25 Hz. In some examples, the scanning frequency may be greater than or equal to 30 Hz. In this way, IMD 110 may avoid or minimize flicker, e.g., a perception of fluctuation as stimulation is shifted between electrode pairs during the scan.

In some examples, IMD 110 may deliver successive pulses via different electrode pairs. In some examples, IMD 110 may deliver electrical stimulation via the pairs of electrodes at a common amplitude. In other examples, IMD 110 may deliver electrical stimulation via different pairs of electrodes at different amplitudes.

Figure 6:
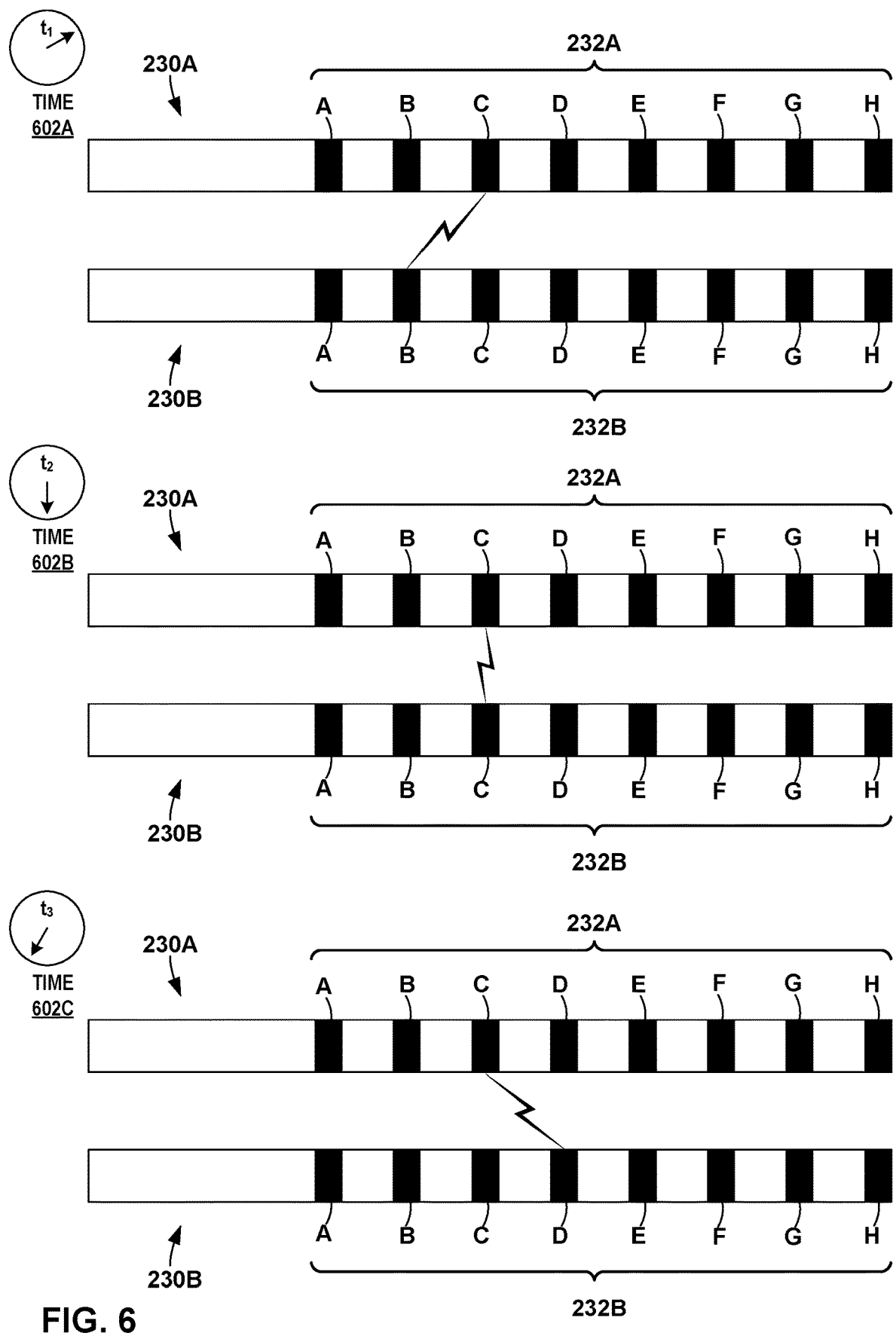
FIGS. 6 and 7 are conceptual diagrams illustrating examples of inter-lead scanning through pairs of electrodes, in accordance with one or more techniques of this disclosure.
Figure 7:
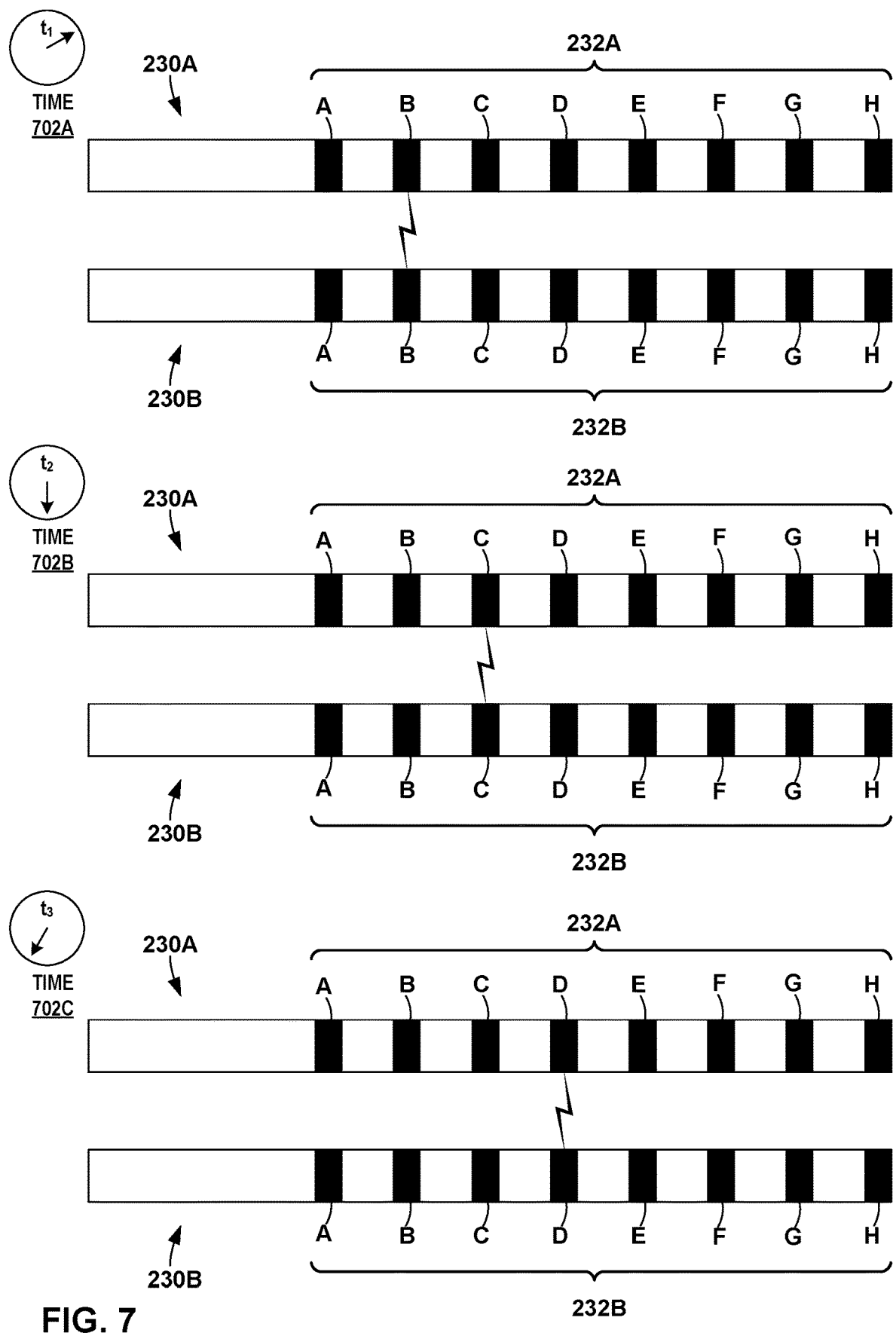

FIGS. 6 and 7 are conceptual diagrams illustrating examples of inter-lead scanning through pairs of electrodes, in accordance with one or more techniques of this disclosure. As discussed above (e.g., with respect to FIGS. 4 and 5), IMD 110 may scan through pairs of electrodes on a particular lead. As shown in FIG. 6, IMD 110 may scan through pairs of electrodes across two leads (e.g., a pair of electrodes that includes a first electrode on a first lead and a second electrode on a second lead). For instance, IMD 110 may scan delivery of bipolar stimulation through a set of electrodes of the first plurality of electrodes and a particular electrode of the second plurality of electrodes. In this way, IMD 110 may effectively scan delivery of stimulation in two dimensions in the case of electrode pairs selected across two leads, or possibly three dimensions in the case of electrode pairs selected across three or more leads. It is understood that the electrodes selected for inter-lead scanning may be monotonic or non-monotonic, as discussed above.

Figure 8:
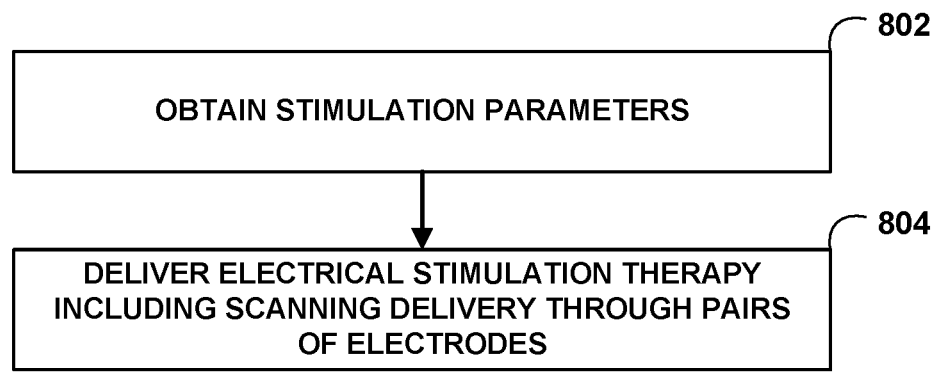
FIG. 8 is a flow diagram illustrating an example method of titrating a therapy, in accordance with one or more techniques of this disclosure.

FIG. 8 is a flow diagram illustrating an example method of titrating a therapy, in accordance with one or more techniques of this disclosure. Although FIG. 8 is discussed using IMD 200 (FIG. 2), it is to be understood that the methods discussed herein may include and/or utilize other systems and methods in other examples.

IMD 200 may obtain one or more stimulation parameters (802). For instance, processing circuitry 210 may obtain one or more of an amplitude, duty cycle, pulse width, etc. from stimulation parameter settings 242.

IMD 200 may deliver, based on the one or more stimulation parameters, electrical stimulation therapy including scanning delivery of stimulation through different pairs of electrodes of a plurality of electrodes (804). For instance, electrode scanning unit 216 may cause stimulation circuitry 202 and switch circuitry 204 to deliver, at a first time, bipolar electrical stimulation via a first pair of electrodes of the plurality of electrodes (e.g., via electrodes A and B of electrodes 232A), and deliver, at a second time that is different than the first time, bipolar electrical stimulation via a second pair of electrodes of the plurality of electrodes (e.g., via electrodes B and C of electrodes 232A). In this manner, IMD 200 may move a stimulation field between different positions as a function of the electrode pairs selected for delivery of stimulation. Electrode scanning unit 216 may cause delivery of an interleaved bipolar cascade of electrical stimulation.

In some examples, IMD 200 may utilize various techniques to reduce a quantity of pairs included in the scan. For instance, IMD 200 may utilize evoked compound action potentials (ECAPs) to determine which pairs of electrodes are most proximate (e.g., overlying) a stimulation target (e.g., nerve root). In operation, IMD 200 may deliver stimulation via various pairs of electrodes and sense (e.g., via electrodes on a lead implanted more medially) whether an ECAP resulted from the delivery. If delivery of electrical stimulation via a particular pair of electrodes does not result in an ECAP, the particular pair of electrodes may be removed from (or not originally included in) a scan. In some examples, delivery of electrical stimulation via a particular pair of electrodes may only result in an ECAP at certain stimulation levels (e.g., ECAP could be smaller, or could only be evoked at a higher level).

In some examples, IMD 200 may perform selective recording. For instance, ECAPs may be detected in structures that are fairly distant from the site of interest. For instance, IMD 200 may record ECAPs with a tripolar configuration to focus ECAP to the region of interest.

IMD 200 may utilize various other techniques to adjust which pairs of electrodes are included in the scan. For instance, IMD 200 may correlate patient state (e.g., heart rate, respiratory rate, ECAPs, posture, blood flow, temperature etc.) with pairs of electrodes. As one example, responsive to determining that the patient is in a particular state, IMD 200 may deliver electrical stimulation by scanning through a set of pairs of electrodes determined to be suited for the patient state. As such, pairs of electrodes not suited for the patient state may be omitted. In this way, IMD 200 may reduce a quantity of pairs of electrodes included in a scan, which may be desirable.

In some examples, IMD 200 may utilize virtual electrodes when scanning. For instance, each combination may be a multi-polar configuration. Each multipolar configuration may be described by a set of weights (from −1 to 1) associated with each electrode. This set of weights may then change to implement different virtual electrodes. As an example, consider electrodes [1, 2, 3, 4] with weights [−0.5 0.5 0.5 −0.5] constituting a virtual electrode in the middle of 2 and 3 (e.g., electrode 2.5), and virtual electrode [−0.3 0.3 0.7 −0.7] constituting a virtual electrode closer to electrode (e.g., electrode 2.8). IMD 200 may scan through virtual electrodes (e.g., electrode 2.5, electrode 2.8, . . . , etc.).

The following numbered examples may illustrate one or more aspects of this disclosure:

Example 1. A method of delivering electrical stimulation, the method comprising: obtaining, by an implantable medical device (IMD) connected to a lead carrying a plurality of electrodes, one or more stimulation parameters; and delivering, by the IMD and based on the one or more stimulation parameters, electrical stimulation therapy via the plurality of electrodes, wherein delivering the electrical stimulation therapy comprises scanning delivery of the electrical stimulation therapy through different pairs of electrodes of the plurality of electrodes.

Example 2. The method of example 1, wherein scanning delivery of the electrical stimulation therapy through the different pairs of electrodes comprises: delivering, at a first time, bipolar electrical stimulation via a first pair of electrodes of the plurality of electrodes; and delivering, at a second time that is different than the first time, bipolar electrical stimulation via a second pair of electrodes of the plurality of electrodes, different from the first pair of electrodes.

Example 3. The method of example 2, further comprising: delivering, at a third time that is different than the first time and the second time, bipolar electrical stimulation via a third pair of electrodes of the plurality of electrodes, different from the first and second pairs of electrodes.

Example 4. The method of example 2 or example 3, wherein the second pair of electrodes includes an electrode that is included in the first pair of electrodes and an electrode that is not included in the first pair of electrodes.

Example 5. The method of example 2 or example 3, wherein the second pair of electrodes does not include any electrodes that are included in the first pair of electrodes.

Example 6. The method of example 5, wherein at least one electrode not included in the first pair of electrodes or the second pair of electrodes is located on the lead between electrodes of the first pair of electrodes and electrodes of the second pair of electrodes.

Example 7. The method of any preceding example, wherein scanning delivery of the electrical stimulation therapy through the different pairs of electrodes comprises scanning through the pairs of electrodes at a scanning frequency.

Example 8. The method of example 7, wherein the scanning frequency is greater than or equal to 25 Hz.

Example 9. The method of example 8, wherein the scanning frequency is greater than or equal to 30 Hz.

Example 10. The method of any preceding example, wherein the plurality of electrodes are distributed along a longitudinal axis of the lead.

Example 11. The method of any preceding example, wherein the one or more stimulation parameters include a stimulation amplitude.

Example 12. The method of example 11, wherein scanning delivery of the electrical stimulation therapy through the different pairs of electrodes comprises: successively delivering electrical stimulation via the pairs of electrodes at the stimulation amplitude.

Example 13. The method of any preceding example, wherein the lead comprises a first lead carrying a first plurality of electrodes and a second lead carrying a second plurality of electrodes, and wherein scanning delivery of the electrical stimulation therapy through pairs of electrodes comprises: scanning delivery of the electrical stimulation therapy through a set of electrodes of the first plurality of electrodes and a particular electrode of the second plurality of electrodes.

Example 14. The method of example 13, wherein scanning delivery of the electrical stimulation therapy bipolar stimulation through the set of electrodes of the first plurality of electrodes and the particular electrode of the second plurality of electrodes comprises: delivering, at a first time, bipolar electrical stimulation via a first electrode of the first plurality of electrodes and the particular electrode of the second plurality of electrodes; and delivering, at a second time that is different than the first time, bipolar electrical stimulation via a second electrode of the first plurality of electrodes and the particular electrode of the second plurality of electrodes.

Example 15. A system comprising: a memory storing one or more stimulation parameters; and an implantable medical device comprising processing circuitry configured to perform the method of any of examples 1-14.

Example 16. The system of example 15, further comprising a lead carrying a plurality of electrodes.

Example 17. A computer readable medium comprising instructions that when executed cause one or more processors to perform the method of any of examples 1-14.

The techniques described in this disclosure may be implemented, at least in part, in hardware, software, firmware or any combination thereof. For example, various aspects of the described techniques may be implemented within processing circuitry, which may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also form one or more processors or processing circuitry configured to perform one or more of the techniques of this disclosure.

Such hardware, software, and firmware may be implemented, and various operation may be performed within a same device, within separate devices, and/or on a coordinated basis within, among or across several devices, to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components. Processing circuitry described in this disclosure, including a processor or multiple processors, may be implemented, in various examples, as fixed-function circuits, programmable circuits, or a combination thereof. Fixed-function circuits refer to circuits that provide particular functionality with preset operations. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive stimulation parameters or output stimulation parameters), but the types of operations that the fixed-function circuits perform are generally immutable. In some examples, one or more of the units may be distinct circuit blocks (fixed-function or programmable), and in some examples, one or more of the units may be integrated circuits.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash

What is claimed is:

1. A method of delivering electrical stimulation, the method comprising:
   obtaining, by an implantable medical device (IMD) connected to one or more leads carrying a plurality of electrodes across the one or more leads, one or more stimulation parameters; and
   delivering, by the IMD and based on the one or more stimulation parameters, electrical stimulation therapy to a spinal cord of a patient via the plurality of electrodes, wherein delivering the electrical stimulation therapy comprises scanning delivery of the electrical stimulation therapy through different pairs of electrodes, wherein the scanning delivery of the electrical stimulation therapy through the different pairs of electrodes comprises scanning through the pairs of electrodes at a scanning frequency of greater than or equal to 25 Hz, and wherein each of the different pairs of electrodes comprises two electrodes of the plurality of electrodes carried across the one or more leads or one electrode of the plurality of electrodes carried across the one or more leads and an electrode on a housing of the IMD.

2. The method of claim 1, wherein scanning delivery of the electrical stimulation therapy through the different pairs of electrodes comprises:
   delivering, at a first time, bipolar electrical stimulation via a first pair of electrodes; and
   delivering, at a second time that is different than the first time, bipolar electrical stimulation via a second pair of electrodes, different from the first pair of electrodes.

3. The method of claim 2, further comprising:
   delivering, at a third time that is different than the first time and the second time, bipolar electrical stimulation via a third pair of electrodes, different from the first and second pairs of electrodes.

4. The method of claim 2, wherein the second pair of electrodes includes an electrode that is included in the first pair of electrodes and an electrode that is not included in the first pair of electrodes.

5. The method of claim 2, wherein the second pair of electrodes does not include any electrodes that are included in the first pair of electrodes.

6. The method of claim 5, wherein at least one electrode not included in the first pair of electrodes or the second pair of electrodes is located on one of the one or more leads between electrodes of the first pair of electrodes and electrodes of the second pair of electrodes.

7. The method of claim 1, wherein the scanning frequency is greater than or equal to 30 Hz.

8. The method of claim 1, wherein the plurality of electrodes are distributed along a longitudinal axis of a lead of the one or more leads.

9. The method of claim 1, wherein the one or more stimulation parameters include a stimulation amplitude.

10. The method of claim 9, wherein scanning delivery of the electrical stimulation therapy through the different pairs of electrodes comprises:
    successively delivering electrical stimulation via the pairs of electrodes at the stimulation amplitude.

11. The method of claim 1, wherein the one or more leads comprise a first lead and a second lead, wherein the first lead carries a first set of electrodes of the plurality of electrodes and the second lead carries a second set of electrodes of the plurality of electrodes, wherein scanning delivery of the electrical stimulation therapy through pairs of electrodes comprises:
    scanning delivery of the electrical stimulation therapy through the first set of electrodes and a particular electrode of the second set of electrodes.

12. The method of claim 11, wherein scanning delivery of the electrical stimulation therapy bipolar stimulation through the first set of and the particular electrode of the second set of electrodes comprises:
    delivering, at a first time, bipolar electrical stimulation via a first electrode of the first set of electrodes and the particular electrode of the second set of electrodes; and
    delivering, at a second time that is different than the first time, bipolar electrical stimulation via a second electrode of the first set of electrodes and the particular electrode of the second set of electrodes.

13. A system comprising:
    a memory storing one or more stimulation parameters; and
    an implantable medical device (IMD) configured to connect to one or more leads carrying a plurality of electrodes across the one or more leads, the IMD comprising processing circuitry configured to:
       obtain one or more stimulation parameters; and
       deliver, by the IMD and based on the one or more stimulation parameters, stimulation signals to the plurality of electrodes which outputs electrical stimulation therapy to a spinal cord of a patient via the plurality of electrodes, wherein, to deliver the stimulation signals, the processing circuitry is configured to scan delivery of the stimulation signals through different pairs of electrodes at a scanning frequency of greater than or equal to 25 Hz, wherein each of the different pairs of electrodes comprises two electrodes of the plurality of electrodes carried across the one or more leads or one electrode of the plurality of electrodes carried across the one or more leads and an electrode on a housing of the IMD.

14. The system of claim 13, wherein, to scan delivery of the stimulation signals through the different pairs of electrodes, the processing circuitry is configured to:
    deliver, at a first time, the stimulation signals for bipolar electrical stimulation via a first pair of electrodes; and
    deliver, at a second time that is different than the first time, the stimulation signals for bipolar electrical stimulation via a second pair of electrodes, different from the first pair of electrodes.

15. The system of claim 14, wherein the second pair of electrodes includes an electrode that is included in the first pair of electrodes and an electrode that is not included in the first pair of electrodes.

16. The system of claim 14, wherein the second pair of electrodes does not include any electrodes that are included in the first pair of electrodes.

17. The system of claim 16, wherein at least one electrode not included in the first pair of electrodes or the second pair of electrodes is located on one of the one or more leads between electrodes of the first pair of electrodes and electrodes of the second pair of electrodes.

18. The system of claim 13, further comprising the one or more leads, wherein the one or more leads comprise a first lead and a second lead, wherein the first lead carries a first set of electrodes of the plurality of electrodes and the second lead carries a second set of electrodes of the plurality of electrodes, wherein to scan delivery of the stimulation signals through pairs of electrodes, the processing circuitry is configured to:

scan delivery of the stimulation signals through the first set of electrodes and a particular electrode of the second set of electrodes.

19. The system of claim 18, wherein, to scan delivery of the stimulation signals, the processing circuitry is configured to:

deliver, at a first time, the stimulation signals for bipolar electrical stimulation via a first electrode of the first set of electrodes and the particular electrode of the second set of electrodes; and deliver, at a second time that is different than the first time, the stimulation signals for bipolar electrical stimulation via a second electrode of the first set of electrodes and the particular electrode of the second set of electrodes.

20. A system comprising:

a memory storing one or more stimulation parameters; and an implantable medical device (IMD) comprising processing circuitry configured to:

obtain one or more stimulation parameters; and deliver, by the IMD and based on the one or more stimulation parameters, stimulation signals to a plurality of electrodes on a lead connected to the IMD which outputs electrical stimulation therapy to a spinal cord of a patient via the plurality of electrodes, wherein, to deliver the stimulation signals, the processing circuitry is configured to scan delivery of the stimulation signals through different pairs of electrodes of the plurality of electrodes at a scanning frequency of greater than or equal to 25 Hz.

\* \* \* \* \*